United States Patent [19]
Wuchinich et al.

[11] Patent Number: 4,787,247
[45] Date of Patent: Nov. 29, 1988

[54] SCANNING APPARATUS AND METHOD

[75] Inventors: David G. Wuchinich, New York; William Henriksen, Happauge; Robert Brendolan, Mamaroneck; Louis Katz, Flushing, all of N.Y.

[73] Assignee: Sonomed Technology, Inc., Lake Success, N.Y.

[21] Appl. No.: 3,157

[22] Filed: Jan. 14, 1987

Related U.S. Application Data

[63] Continuation-in-part of Ser. No. 888,660, Jul. 23, 1986, abandoned.

[51] Int. Cl.$^4$ .............................................. G01N 29/00
[52] U.S. Cl. ................................. 73/620; 128/660.10; 73/633
[58] Field of Search .................. 73/620, 633, 618, 619, 73/634, 866.5, 629; 128/660; 367/104; 342/158; 343/766; 358/112, 199, 208; 74/89.22

[56] References Cited

U.S. PATENT DOCUMENTS

| | | | |
|---|---|---|---|
| 4,317,370 | 3/1982 | Glenn | 73/620 |
| 4,462,255 | 7/1984 | Guess et al. | 73/633 |
| 4,515,017 | 5/1985 | McConaghy | 73/618 |
| 4,632,501 | 12/1986 | Glynn | 324/80 |
| 4,649,925 | 3/1987 | Dow et al. | 73/620 |
| 4,682,498 | 7/1987 | Kreiskorte | 73/633 |

Primary Examiner—John Chapman
Attorney, Agent, or Firm—Pennie & Edmonds

[57] ABSTRACT

A scanning apparatus and method for scanning an object including a frame, a transducer for obtaining information from an object and a motor oscillating the transducer. The motor comprises a spring/solenoid combination driven at the resonant frequency of the spring/motor system. The actual displacement of the transducer is measured and compared to a desired displacement to provide a control signal to the motor. The scanning apparatus is at least partially enclosed by a housing containing a heat transfer fluid for damping the resonant vibration of the apparatus.

54 Claims, 9 Drawing Sheets

FIG. 8
PHASE RELATION BETWEEN
SOLENOID FORCE AND EXCURSION
FOR FREQUENCIES f

FIG. 9
SOLENOID POWER CONSUMPTION
AS A FUNCTION OF $x = \pi t_0/T$

FIG. 10

PHASE RELATIONSHIPS BETWEEN ERROR
SIGNALS AND COMPARATOR CONTROL SIGNALS
($e_{C-1}$, $e_{C-2}$) AND OUTPUTS ($e_{0-1}$, $e_{0-2}$)

SCANNING APPARATUS AND METHOD

CROSS REFERENCE TO RELATED APPLICATIONS

This application is a continuation-in-part of application Ser. No. 888,660, filed July 23, 1986, now abandoned.

TECHNICAL FIELD

The present invention relates to a scanning apparatus and method for scanning an object. More specifically, the invention relates to the use of a hand-held ultrasonic scanning device for the examination of the human eye or other relatively small organs.

BACKGROUND ART

Diagnostic ultrasonic scanning systems commonly rotate an ultrasonic transducer back and forth through a prescribed angle (sector) while rapidly transmitting high frequency sound waves into a biological structure. Thereafter, the reflected waves are received and processed to generate a two dimensional cathode ray tube display of the biological morphology revealed by the intensity and origin of the echos received.

The reciprocal transducer motion required in such scanning must be (1) of stable and repeatable amplitude and (2) of substantially constant frequency. A variety of mechanisms have been employed to generate motion with the requisite features. Motor driven cam actuators, cranks and eccentrics as well as stepping motors have been used successfully in probes for such scanning devices, but the recent development of low cost, high speed scan converters which permit high resolution displays on inexpensive television monitors have imposed an additional constraint upon the scan head frequency. Since the frame rate used in television system is fixed precisely at 30 Hz in the U.S., echo data must be received and processed synchronously with this frequency if, as is normally required in diagnostic medical examinations, the display is to instantly reflect the probe application.

It is possible to employ A.C. synchronous motors to achieve the required scan frequency precision, but such A.C. motors are relatively large compared to the D.C. motors which have previously been used. Also, probes incorporating such A.C. motors are bulky and difficult to manipulate in diagnostic procedures: particularly in those examinations of relatively small organs such as the eye. Stepper motors can also be operated to provide a specified scan frequency, but their motion is not continuous. In high resolution ultrasonography, the use of a discontinuous, stepped scan head motion can itself limit the resolution of signal processing circuitry that may be capable of revealing finer detail than the number of discrete motional steps permitted by the motor. Stepper motors are also larger than D.C. motors having the same power output and inevitably limit a reduction in probe size.

Because none of the existing probe designs could satisfy the need for a small hand held probe operating at a precisely predetermined frequency with a well controlled amplitude, a new mechanism was developed that has the required features with not intrinsic limit to miniaturization.

SUMMARY OF THE INVENTION

This invention relates to a scanning apparatus comprising means for obtaining information from an object and means for oscillating the information obtaining means to scan a predetermined portion of the object. The information obtaining means is preferably an ultrasonic transducer, while the object is usually a relatively small biological organ, such as an eye.

The oscillation means generally comprises frame means and means for connecting the frame means to the information obtaining means. The connecting means includes first means for providing reversible forces to the connection means, means for measuring the displacement of a portion of the connection means in response to forces provided thereto, means for comparing the measured displacement of the connection means portion with a predetermined desired displacement, and second means for providing reversible forces to the connection means to compensate for the difference between the measured displacement and the predetermined desired displacement.

The apparatus may also include housing means, and means for mounting the oscillation means and information obtaining means to the housing means. If desired, resonant frequency adjusting means, preferably in the form of screw means on the object information obtaining means or collar means on the force providing means, can be provided for "fine-tuning" the apparatus before use. Also, the free spaces of the housing are filled with a heat transfer fluid to dampen the resonant vibration of the apparatus.

Preferably, the first reversible force providing means is spring means which provides linear movement and is attached to the frame. The means for measuring the displacement of the connection means may be transformer means or force sensing means, such that the comparison means may be a comparator circuit. In response to the detected difference between the measured displacement and desired displacement, forces are provided to the connection means, preferably by solenoid means, to cause the measured displacement to correspond to the desired displacement.

The invention also relates to methods of adjusting the resonant frequency of the apparatus or scanning an object by utilizing these apparatus.

BRIEF DESCRIPTION OF THE DRAWINGS

These and other objects, features and advantages of the present invention will be more readily apparent from the following detailed description of preferred embodiments of the invention in which.

DETAILED DESCRIPTION OF THE PREFERRED EMBODIMENTS

Figure 1:
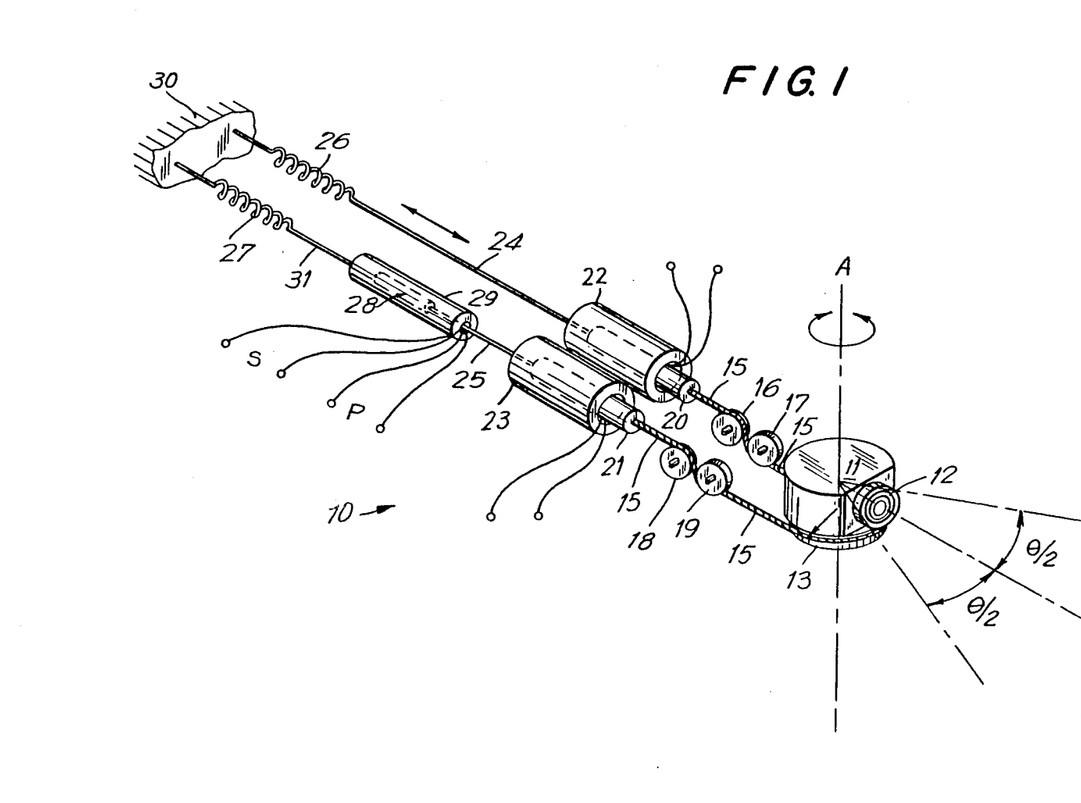
FIG. 1 is a perspective view of a side scanning apparatus according to the invention.

Briefly, the scanning probe of the invention uses mechanical resonance to produce reciprocal motion of the scanning head. This motion is initiated and sustained by two solenoids that alternately exert a force commensurate with the scan head excursion desired and the mechanical loading imposed upon the moving elements. A proposed theory for this mode of operation follows: the interconnected elements of a preferred probe are shown in FIG. 1. Mathematically, the motion of this system can be expressed as $$F(t) = \left(M_T + \frac{J_M}{R^2}\right)\frac{d^2x}{dt^2} + \eta \frac{dx}{dt} + (K_R + K_L)x \quad (1)$$

where x is the excursion of the cable from its equilibrium position, $\eta$ is the damping factor which includes the friction and viscous forces (if any) present, $K_R$ and $K_L$ are the spring constants, R is the radius of the scan rotor pulley, $J_M$ is the polar moment of inertia of the scan rotor, $M_T$ is the sum of solenoid armatures, linear variable distance transformer (LVDT), core and cable masses, and F(t) is the imposed (solenoid) force.

The resonant frequency or the frequency at which the system vibrates naturally when momentarily disturbed is the frequency of the harmonic solution to Eq. 1 when both F(t) and $\eta$ are zero, namely:

$$f_o = \frac{1}{2\pi}\sqrt{\frac{K_R + K_L}{\left(M_T + \frac{J_M}{R^2}\right)}} \quad (2)$$

Since to operate the system, F(t) must be a periodic function of time, and it may be expressed as a Fourier series. Normally, only the first frequency component (fundamental) of this force is predominant and effective in powering the motion, and with $F(t) = Fe^{j\omega t}$, the solution becomes:

$$F = A\left[-\left(M_T + \frac{J_M}{R^2}\right)\omega^2 - j\omega\eta + (K_R + K_L)\right] \quad (3)$$

where A is the amplitude of the excursion and F is the amplitude of the fundamental component of the imposed force. We find from Eq. 3 that:

$$F = -\left[1 + jQ\left(\frac{\omega}{\omega_0} - \frac{\omega_0}{\omega}\right)\right]A\omega\eta j \quad (4)$$

where Q, $2\pi$ times the ratio of the maximum energy stored in the kinetic energy of the mass motion (or the maximum energy stored in the springs) to the energy lost per cycle of oscillation, is:

$$Q = \frac{\omega_0\left(M_T + \frac{J_M}{R^2}\right)}{\eta}$$

and the angular frequency of resonance, $\omega_o$, is:

$$\omega_0 = \sqrt{\frac{K_R + K_L}{\left(M_T + \frac{J_M}{R^2}\right)}}$$

As Eq. 4 shows, at $\omega = \omega_o$, F lags the actual excursion by $\pi/2$ radians or 90 degrees. Consequently, if the solenoids are alternately pulsed on and off to provide a driving force whose principal component is F, the center of these pulses coincides in time with the point at which the scan head passes through its equilibrium position (or the point of maximum excursion velocity). If $Q >> 1$, this phase relationship changes rapidly for driving frequencies slightly above or below $\omega_o$.

The mechanical power required to maintain oscillation is:

$$P_M = F\frac{dx}{dt} \quad (5)$$

Since in Eq. 1, the only term which results in a non-zero time averaged product with F is $$\eta \frac{dx}{dt},$$

the real average power would be:

$$P_M = \frac{1}{2}\eta\left(\frac{dx}{dt}\right)^2 \quad (6)$$

$$P_M = \frac{1}{2}\eta(A\omega)^2 \quad (7)$$

However, the electrical power requirement is proportional to the square of the solenoid voltage which, in turn, is approximately proportional to the solenoid force. As shown in Eq. 4, F is a minimum at $\omega = \omega_o$ and, depending upon the magnitude of Q, becomes progressively larger as the angular frequency departs from $\omega_o$:

$$|F| = \eta\omega A\left[1 + Q^2\left(\frac{\omega}{\omega_o} - \frac{\omega_o}{\omega}\right)^2\right]^{\frac{1}{2}} \quad (8)$$

Then, the electrical power required is:

$$P_E \alpha \ \eta\omega A\left[1 + Q^2\left(\frac{\omega}{\omega_o} - \frac{\omega_o}{\omega}\right)^2\right]^{\frac{1}{2}} \quad (9)$$

If $Q >> 1$, the electrical power required to maintain a fixed excursion rapidly increases for $|\omega - \omega_o| > 0$. Since the scan frequency, $f_s$, is predetermined, it is obviously advantageous to adjust $M_T$, $J_M/R^2$, $K_R$ and $K_L$ to make $f_o \approx f_s$. However, variations in spring constants make such effort only approximate. To preclude large electrical losses for values of $f_o$ slightly different from $f_s$, Q must be restrained.

Fortunately, mechanical losses both from friction in the bending action of the connecting cable and from the movement the movement of the scan head, solenoid armatures and LVDT core through the transducer acoustic coupling fluid, in which the entire assembly is immersed, limit Q normally to no more than about 2. Then, from Eq. 9:

$$P_E/_{f=f_s} = 2\, P_E/_{f=f_o}$$

$$\text{when } \frac{|f_s - f_o|}{f_o} \geq \frac{1}{2}\,;\, Q = 2$$

The electrical power doubles when $$f_s \leq \frac{1}{\sqrt{2}} f_o \text{ or when } f_s \geq \left(2 - \frac{1}{\sqrt{2}}\right) f_o$$

With $f_o = 15$ Hz, for example, $P_E$ is doubled, with Q=2, at $f_s = 10$ or 19 Hz.

Referring now to FIG. 1, there is illustrated a preferred ultrasonic scanning apparatus 10 according to the present invention.

This apparatus includes a cylindrical scanning head 11 mounted on a vertical axis A—A for rotation thearoud through a predetermined angle. This head 11 includes an ultrasonic transducer 12 for obtaining information from the object to be scanned. Although the invention is advantageously designed for use with ultrasonic transducers, for scanning in the B-mode, it will be appreciated by those skilled in the art that other information obtaining means, such as radar, electromagnetic, optical, visual, or acoustic means, could be used for specific applications.

The scanning head 11 includes a pulley 13 for engaging a driving cable 15 which causes the head 11 to oscillate. This cable is directed through guide pulleys 16, 17, 18 and 19, and the ends of the cable 15 are attached to front ends of the respective central cores, 20, 21, of first and second solenoids, 22, 23. The solenoids 22, 23 each include a cylindrical winding through which the respective central cores 20, 21 oscillate.

The rear ends of the central cores are attached to cables 24, 25. The calbe 24 extending from the first solenoid central core 20 is attached to a spring 26 which, in turn, is attached to the frame 30 of the apparatus 10. The cable 25 extending from the second solenoid central core 21 is attached to the front of the central core 28 of a linear variable differential transformer (LVDT) 20. The LVDT 29 includes cylindrical primary and secondary windings through which the central core 28 oscillates. The primary winding of the LVDT 29 is used to power the LVDT, while the secondary winding is used to determine the position of the central core 28. Another cable 31 is attached to the rear of the LVDT central core 28 and extends to a spring 27 which is also attached to frame 30.

Figure 7:
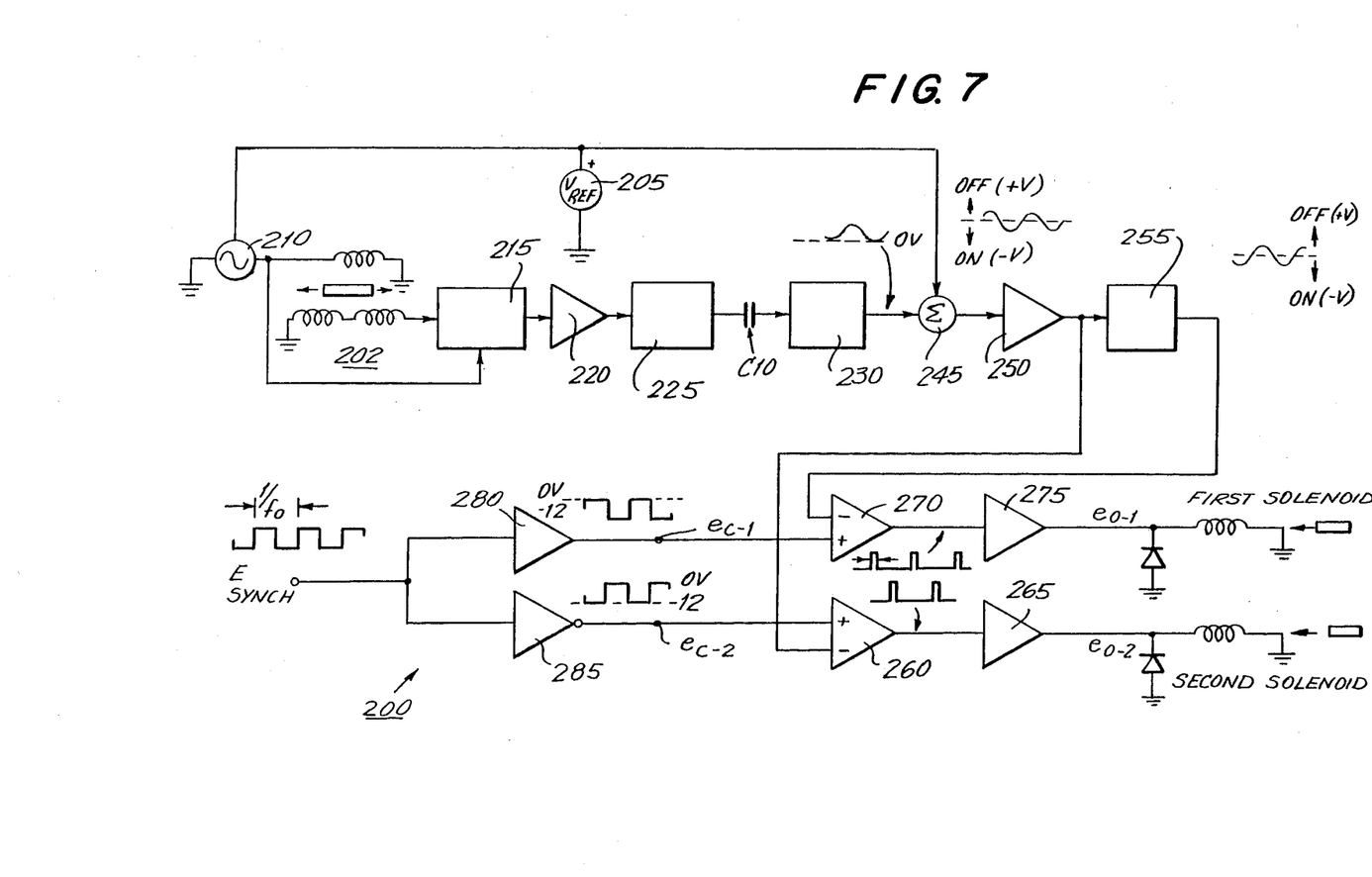
FIG. 7 is a block diagram of a servo for the scanning apparatus of the invention.

A preferred comparator circuit block diagram is shown in FIG. 7 and is explained in detail hereinbelow.

This apparatus 10 operates as follows: when the unit is turned on, the LVDT 29 senses no movement, so that the predetermined pulse train causes the first solenoid 22 to operate. This solenoid 22 retracts its central core 20, thus pulling cable 15 and causing scanning head 11 to rotate an angle less than $\theta/2$ and correspondingly causing central core 21 to be moved forward. This, in turn causes the central core 28 of the LVDT to also be moved forward, while spring 27 is extended and spring 26 is compressed. The LVDT 29 measures the displacement of the core 28 and this information is utilized by the comparator circuit to determine the difference between the actual and desired displacement values. This differential pulse is then applied to activate the second solenoid which retracts its central core 21, thus pulling cable 15 in the opposite direction. Accordingly, spring 26 is extended, spring 27 is compressed, central core 20 is extended, and central core 28 is retracted, with scanning head 11 being rotated through angle approaching a steady state valve of $\theta$. Thereafter, the sequence repeats, with an oscillation of the transducer 12 through steady state angle $\theta$ being obtained for each step.

As one skilled in the art will realize, the resonant frequency of the system due to the inertia of the movement of the scanning head 11 in combination with the elasticity of the spring 26, 27 provides reversible forces which help maintain the oscillation of the scanning head 11. Therefore, the apparatus 10 requires only a very low amount of energy to oscillate, and this energy is provided by the solenoids 22, 23. Furthermore, this arrangement is ideally suited for miniaturization of the scanning apparatus.

For other applications where the size of the apparatus 10 is not critical, different force providing means can be utilized to obtain the same effect. For example, the primary force providing means, i.e., the springs 26, 27, can be replaced by motors, gears, eccentrics, pulleys or other mechanical devices which are capable of providing the desired reversible motion to the system. Similarly, the secondary force providing means, the solenoids 22, 23, can be replaced by similar devices, with it being recognized that the force provided by the secondary means is significantly lower than that provided by the primary means. Also, other means for measuring displacement, such as piezoelectric senors, magnetic senors, strain gauges, pneumatic sensors, hydraulic sensors or other force sensors can be substituted for the LVDT 29 when the size of this component is not critical. In these variations of the invention, the element for measuring displacement of the cable, i.e., the LVDT 29, and the comparator circuit which is used to direct the operation of the secondary means to provide the incremental power necessary to achieve the desired displacement, are key elements in the operation of the invention.

Figures 2, 3:
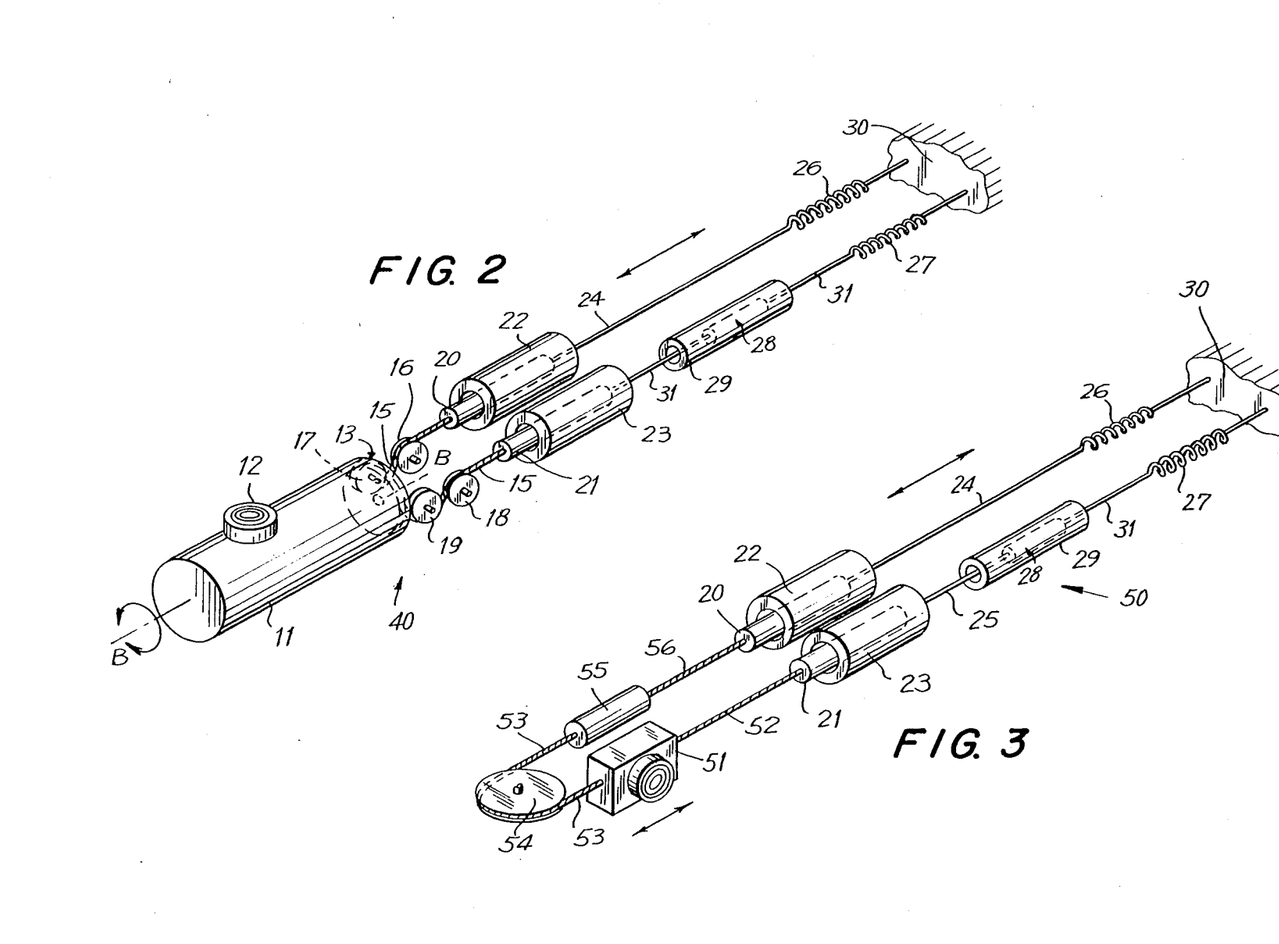
FIG. 2 is a perspective view of a second side scanning apparatus.
FIG. 3 is a perspective view of a linear scanning apparatus.

FIG. 2 shows an apparatus 40 similar to that of FIG. 1, and the same numerals are used to describe parts which function in the same way. The main difference between the apparatus 40 of FIG. 2 and that of FIG. 1 is that the scanning head 11 and scanning pulley 13 are mounted perpendicular to the position of FIG. 1. This enables the scanner to rotate about a horizontal axis B—B.

FIG. 3 illustrates another apparatus 50 which is similar to FIGS. 1 and 2 in that components 20 through 31 are the same. In this apparatus 50, the front end is modified to provide oscillating linear movement of the scanning head 51, as shown. To accomplish this, cable 52 connects the front end of solenoid central core 21 to one side of the scanning head 51. The opposite side of the scanning head 51 is attached by cable 53, which passes around pulley 54, to the front end of a counterweight 55.

The opposite end of the counterweight 55 is attached by cable 56 to the front end of solenoid central core 20. The oscillating motion of the solenoid cores 20, 21 produces the linear oscillation of the scanning head 51.

Figures 4, 5, 6:
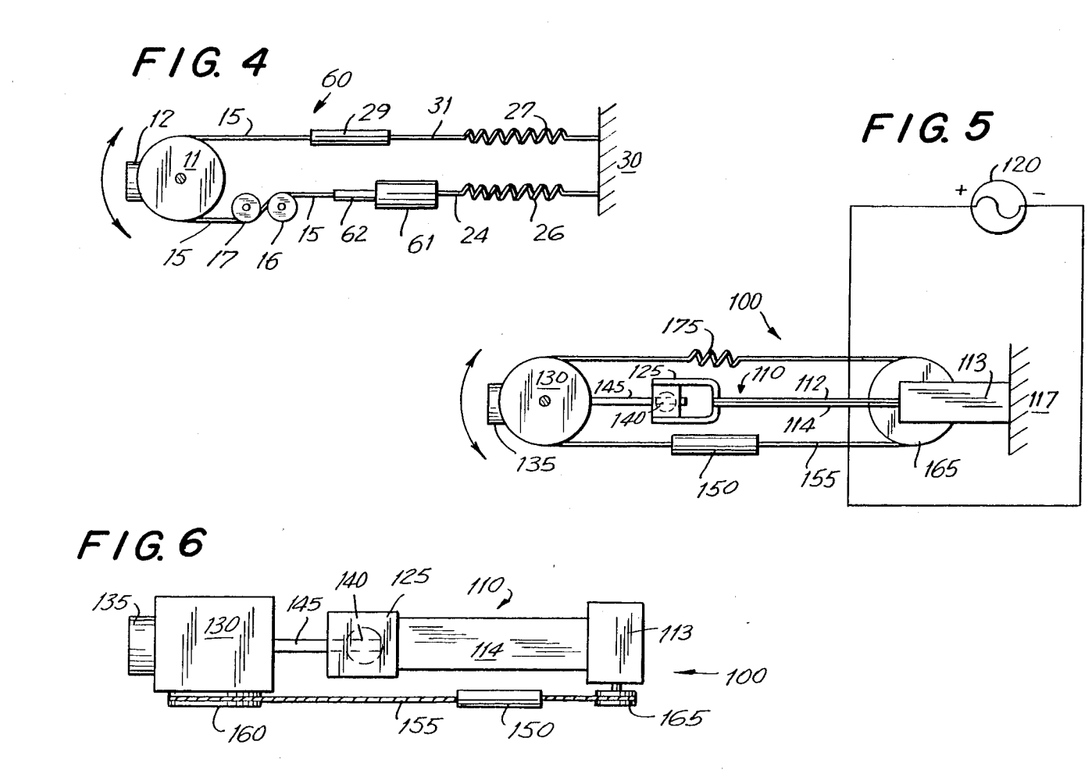
FIG. 4 is a perspective view of a single solenoid resonant scanning apparatus.
FIG. 5 is a top view of a bimorph driven resonant scanning apparatus.
FIG. 6 is a side view of the apparatus of FIG. 4.

FIG. 4 shows another embodiment of the invention, again utilizing similar elements as in FIGS. 1-3, except that the dual solenoid arrangement of those FIGS. is replaced with a single solenoid 61 having central core 62 and which is capable of generating reciprocal (i.e., push-pull) forces. This further simplifies the invention.

One skilled in the art can contemplate further modifications on this single solenoid arrangement. For example, by replacing cables 24 and 15 with a rod, and by moving the LVDT 29 to the opposite side, it would be possible to utilize a single stroke linear system. Other variations are also possible where size and power requirements are not critical to the overall apparatus.

FIGS. 5 and 6 illustrates a further modification of the apparatus 100 wherein a bimorph 110, consisting of support 113, upper electrode 112 and lower electrode 114, vibrates in response to applied voltages oscillator 120. The bimorph support 113 is mounted to a frame 117. Vibration of the bimorph 110 cause yoke 125 to corresponding vibrate, thus causing rotation of the scanning head 130 (and transducer 135) through pivot 140 and pin 145. An LVDT 150 is used to measure the displacement of cable 155, which cable connects the scan head pulley 160 and idler pulley 165. This cable 155 also is connected to a tension spring 175.

As this apparatus 100 operates, the LVDT 150 measures the actual displacement of cable 155, while a comparator circuit, similar to 200, of FIG. 7, compares this value to a predetermined desired value, and thus varies the change in voltage of the voltage oscillator 120, which in turn produces a vibration of the bimorph 110 to correspond the actual cable displacement with the desired displacement.

The scan servo of the presently preferred embodiment automatically controls the scan head excursion, maintaining the probe sector angle at a predetermined value. As shown in FIG. 1, the cable displacement (and hence scan head angle) is sensed by a miniature linear variable differential transformer (LVDT). The transformer's secondary voltage, when properly processed, provides a voltage whose magnitude is exactly proportional to the cable excursion or displacement. This signal is used to provide both an indication of head movement as well as a means for controlling this movement.

Since the scan frequency is fixed, the servo generally operates the probe at this fixed frequency while maintaining a preferably fixed excursion. To obtain the required performance, the servo must (1) regulate the excursion with sufficient speed to prevent variations in the scan angle, due to varying loads and variations in the characteristics of the probe components, from being noticeable and (2) provide an electrical drive that minimizes electrical power dissipation in the solenoids and therefore also minimizes an operating temperature rise of the probe due to this dissipation.

Figure 8:
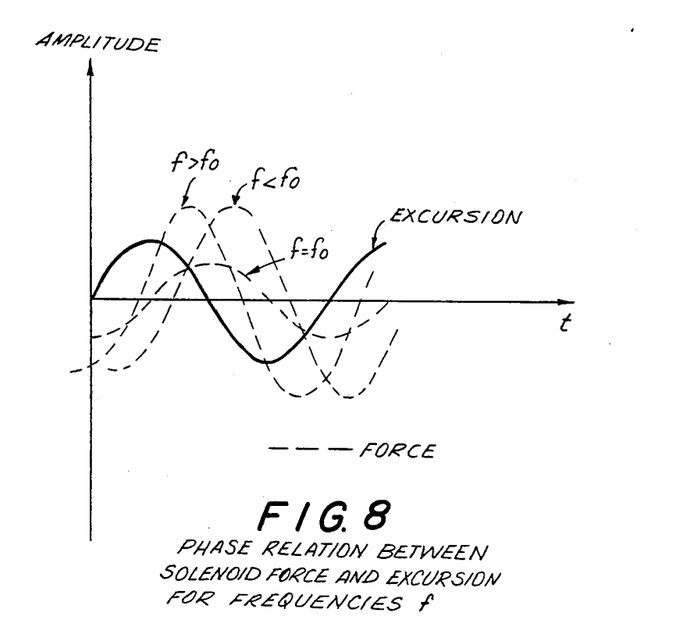
FIG. 8 is a graph of the phase relation between solenoid force and excursion for certain frequencies.

As Eq. 4 shows, at resonance, the solenoid force lags the excursion by 90 degrees. FIG. 8 illustrates the relationship between the force and excursion for values of scan head frequency equal to, above and below $f_o$. For values of $f < f_o$, the force is a maximum when the scan head is decelerating. For $f > f_o$, the force is a maximum during the time when the head is accelerating. Although at $f = f_o$ the force required is a minimum, this situation is difficult to maintain since $f_o$ depends upon the scan head dimensions and the spring constants. FIG. 7 makes clear that attempts to regulate the excursion, x, by controlling the amplitude of F can only be stably accomplished be ensuring that f always lies above $f_o$ or, if the solenoid drive is reversed (replacing F by $-F$ in Eq. 4), that f always lies below $f_o$. Control of the excursion amplitude for scan frequencies close to $f_o$ will in general result in instability, particularly for situations where the losses are small ($Q \gg 1$).

The preferable method of providing an electrical drive to the solenoids is to power each with square waves of frequency f, separated in phase by 180 degrees, whose amplitude the servo controls. A more efficient alternate embodiment operates the probe solenoids by pulses, again separated in phase by 180 degrees, of constant amplitude but whose width is adjusted to provide the required regulating force.

The solenoid power dissipation due to a square wave pulse train of amplitude V, period T and pulse width $t_o$ is proportional to the square of the rms value of this pulse train, and is calculated as follows:

$$V^2_{rms} = V^2 \left( \frac{t_o}{T} \right) \quad (10)$$

The amplitude of a first frequency component, i.e., fundamental, of the Fourier series representation for this pulse train can also be shown to be:

$$V_1 = \frac{2}{\pi} V \sin(\pi t_o/T) \quad (11)$$

Figure 9:
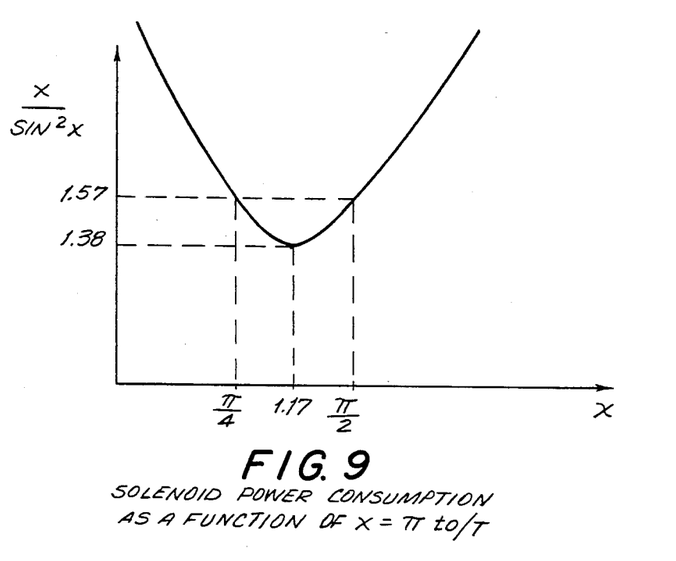
FIG. 9 is a graph of solenoid power consumption.

$V_1$ provides the principal force component actuating the probe. For a given sector angle, $V_1$ preferably is a constant regardless of the ratio $t_o/T$. Consequently, from Eqs. 10 and 11, $$V^2_{rms} = \frac{\pi}{4} V_1^2 \frac{(\pi t_o/T)}{\sin^2(\pi t_o/T)} \quad (12)$$

since $V_1$ is a constant, $V_{rms}^2$ varies as $x/\sin^2 x$ where $x = \pi t_o/T$. This function is plotted in FIG. 9. As FIG. 9 shows, and hence solenoid dissipation is a minimum value of 1.38 when $x = 1.17$ radians ($\pi t_o/T = 67$ degrees) and increases to 1.57 for $t_o/T = \frac{1}{2}$ or $\frac{1}{2}\pi$ radians. The driving pulses to the solenoids are preferably 180 degrees apart and do not change substantially with slight variations in $f_o$ or with pulse width changes required by demands for greater or lesser power.

If a constant amplitude pulse is used, regulation of the actual excursion generally requires that the servo change pulse width rapidly enough to avoid noticeable diminution or expansion of the sector angle. Since the scanned display is visual, this restriction can be satisfied by ensuring that the amplitude frequency response of the servo extend at least to 30 Hz. However, the scan frequency is nominally 15 Hz. It is therefore desirable that the servo respond to sector variations with approximately twice the frequency of scanning. Since amplitude information can be acquired no faster than the scan rate, the servo preferably detects positional information at least every cycle of oscillation.

FIG. 7 is a block diagram 200 of the presently preferred servo scan device. A miniature linear variable differential transformer (LVDT) 202 is provided with primary winding terminals for excitation and secondary winding terminals for position detection. Excitation of the primary winding is provided by a 10 Khz carrier signal whose amplitude is kept constant by a control circuit comprising a stabilized D.C. reference voltage 205 and amplitude stabilized carrier oscillator 210. The output $V_{ref}$ of voltage reference 205 is input to oscillator 210 whose output, along with a ground signal, is input to the primary winding of LVDT 202.

The output of LVDT 202 on its secondary winding is synchronously demodulated by synchronous demodulator 215, amplified by amplifier 220 and then low pass filtered by low pass filter 225 to extract a slowly varying D.C. voltage level proportional to the excursion. The actual D.C. component is removed from this signal by a high pass filter comprising D.C. decoupling capacitor C10 having a cutoff frequency approximately equal to 0.1 Hz. The actual D.C. component is removed to prevent the quiescent transducer head position from adversely affecting the servo mechanism.

Alternately a narrow band pass filter can be utilized at 225 whose center frequency is precisely tuned to the scan frequency to produce a signal level proportional to the excursion. In this embodiment, capacitor C10 is not needed.

The dynamic scan head position signal passed through capacitor C10 (or directly from narrow band pass filter 225) is input to D.C. restorer 230 which clamps the signal's minimum value to zero, thus producing a resultant signal having an essentially D.C. component equal to the average value of the peak to peak excursion and an A.C. component proportional to the actual excursion. This resultant signal is added by summing device 245 to the precise D.C. voltage level $V_{ref}$ produced by D.C. voltage reference 205 controlling the LVDT carrier excitation level. Error amplifier 250 amplifies this difference between actual and desired performance.

The error signal produced by error amplifier 250 is essentially proportional to the excursion with a D.C. component whose magnitude varies with the actual power requirement. This error signal is input to an inverting input of comparator 260. A synchronizing signal $E_{synch}$ of frequency $f_s$ approximately equal to $f_o$ is produced (means not shown) and input to inverter 285, whose comparator control output $e_{c-2}$ is input to a non-inverting terminal of comparator 260. Comparator 260 produces a positive output every time the error signal is less than the perfect square wave of $E_{synch}$ whose amplitude alternates between zero and a negative voltage which the error amplifier cannot reach. The output of comparator 260 is input to driver 265 which drives a second solenoid.

The error signal produced by error amplifier 250 is also input to allpass lag filter 255 which has a gain of $+1.0$ at $f=0$ and a gain of $-1.0$ at $f=f_o$. Filter 255 inverts the A.C. component but does not alter the D.C. component. This phase inverted signal is input to an inverting terminal of comparator 270. Synchronizing signal $E_{synch}$ is input to amplifier 280 whose comparator control output $e_{c-1}$ is input to a non-inverting terminal of comparator 270. This signal is shifted 180 degrees in phase from its corresponding signal input to comparator 260. Comparator 270 functions similarly to comparator 260, producing a positive output when the phase shifted error signal falls below zero volts. The output of comparator 270 is input to driver 275 which drives a first solenoid.

Solenoid drivers 265, 275 produce pulses whose widths are identical and whose centers are spaced 180 degrees apart. Since the error signal intersection with the square wave control signal are determined by the LVDT signal itself, regulation (of pulse width) is preferably performed on a per cycle basis.

Figure 10:
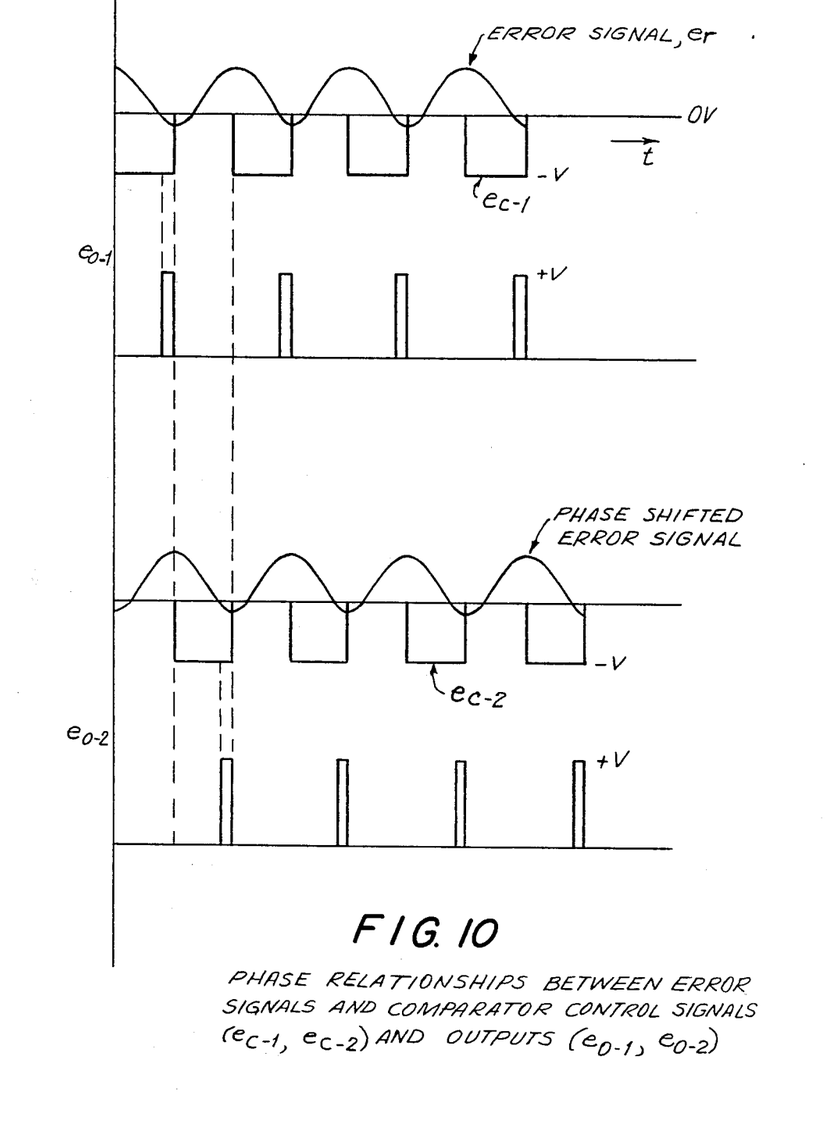
FIG. 10 is a graph of the phase relationships between error, comparator control, and comparator output signals.

FIG. 10 depicts the relationship between the error signals and the two control inputs $e_{c-1}$, $e_{c-2}$ for scan frequencies above resonance ($f>f_o$). As more (or less) power (or pulse width) is required, error amplifier 250 lowers (or raises) the D.C. level, thus resulting in an intersection with the square wave control inputs that widens or reduces the duration of time for which the error signal falls below zero. As mentioned above, the error amplifier's output is limited so that it cannot fall below the negative value of this square wave. Since the outputs of comparators 260,270 constitute the driving signals for the solenoids, this limitation on the most negative value of the error signal ensures that, under operating conditions which require maximum solenoid force, both solenoids cannot be activated continuously. Under maximum power demand, both solenoids are driven by precise square waves.

FIG. 9 shows that probe activation is accomplished with minimum solenoid power dissipation if the pulse width ratio $(t_o/T)$ is 1.17 (or $0.37\pi$). Thus, it is believed that a most efficient alternate embodiment may comprise a servo scheme involving a constant 0.37 duty cycle pulse whose amplitude controls excursion. It is believed that low power consumption may be achieved in such an embodiment by fast amplitude detection on the filtered LVDT signal using synchronous detection at the scan frequency.

Figure 11:
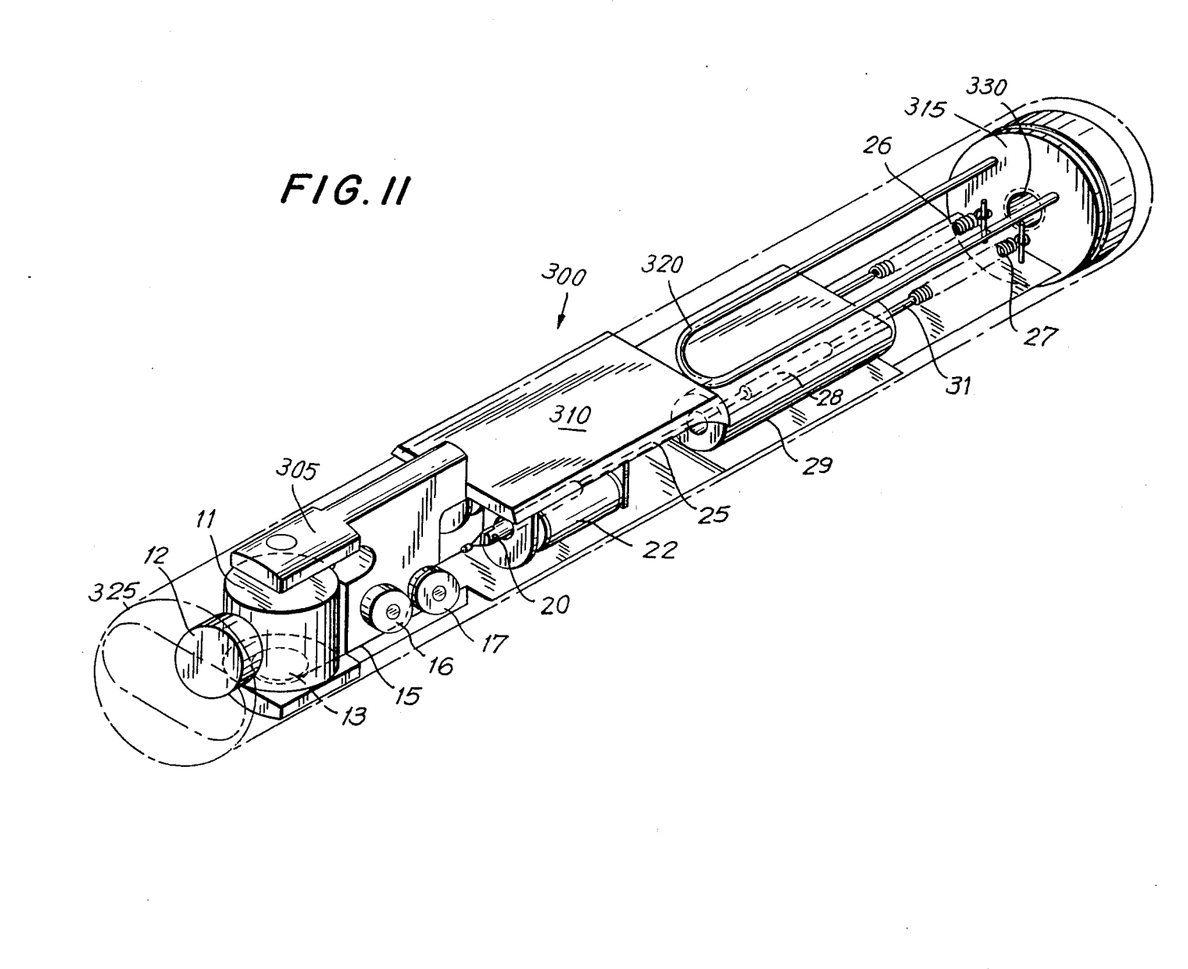
FIG. 11 is a perspective view of the scanner mounted in a housing.

FIG. 11 illustrates a preferred embodiment for a scanning apparatus in a housing 300. In this embodiment, the components which are the same as those of FIG. 1 carry the same numerical designations.

As in FIG. 1, the apparatus has a cylindrical scanning head 11 mounted on a vertical axis and an ultrasonic transducer 12 for obtaining information from the object to be scanned. The scanning head 11 includes a pulley 13 for engaging a driving cable 15 which causes the head 11 to oscillate. This cable is directed through guide pulleys and the ends of the cable are attached to front ends of the respective central cores of first and second solenoids. These solenoids each include a cylindrical winding through which the respective central cores oscillate. The scanning head and guide pulleys are mounted on a frame member 305 in predetermined locations. The solenoids are mounted on an overhead support plate 310.

The rear ends of the central cores are attached to cables. The cable extending from the first solenoid central core is attached to a spring 26 which, in turn, is attached to an end member 315. The cable 25 extending from the second solenoid central core 21 is attached to the front of the central core 28 of a linear variable differential transformer (LVDT), in order to minimize the size of the apparatus. Another cable 31 is attached to the rear of the LVDT central core 28 and extends to a spring 27 which is also attached to end member 315. Frame 305, plate 310, and end member 315 are connected to the housing by a U-shaped support bar 320.

The component parts described above are all encased in a housing 325 (shown in phantom). The entire volume of free space inside the housing is filled with a heat transfer fluid. Although any known heat transfer fluid can be used, propylene glycol, silicone oil or mineral oil based fluids have been found to be the most advantageous. Aside from its primary function of coupling the ultrasonic waves emitted from the transducer 12 to the scanned body member, this heat transfer fluid also serves to dampen the resonant vibration of the unit, thus making it more controllable by the user. The fluid also conducts the heat generated by the solenoids to the housing, thus providing a path for effective cooling. An additional advantage of the fluid is that is provides lubrication for the moving parts of the apparatus.

As the fluid removes heat from the solenoids and other moving parts, its temperature rises and its volume expands. To present an excessive buildup of pressure due to this expansion, a pressure relief device 330 is provided. It is also possible to provide cooling coils to assist in heat removal of the fluid, if desired.

The most preferred cable material for the compact embodiment of FIG. 11 has been found to be a stress relieved monofilament thermoplastic because it reduces the influence of cable elasticity on the resonant frequency of the system.

Figure 12:
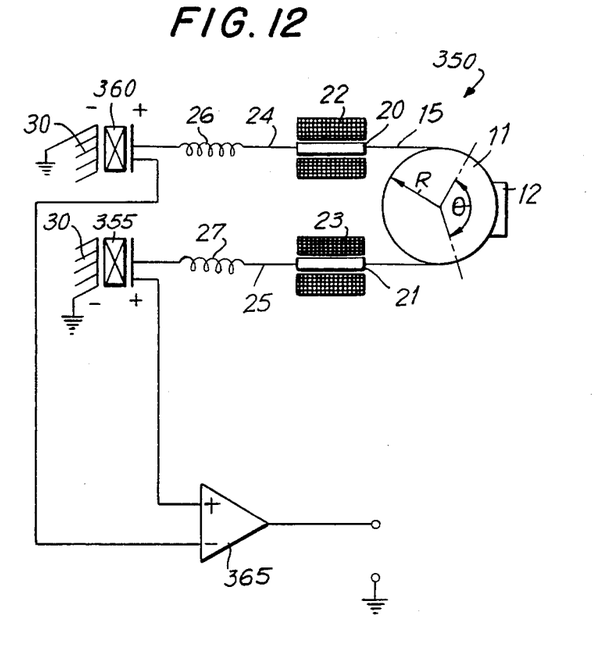
FIG. 12 is a diagram of an embodiment for the scanner which utilizes force sensors.

FIG. 12 illustrates a scanning apparatus 350 which utilizes force sensors 355, 360 instead of the LVDT for measuring the linear displacement of the cable. These force sensors can be made of piezoelectric crystals or other material which are well known to those skilled in the art. This FIG. illustrates how the electric voltage signals produced by such crystals can be processed to produce a signal which is proportional to the scan rotor excursion.

The use of force sensors 355, 360, greatly simplifies the construction of the servo, since the LVDT signal generator and demodulator are not required: only a single comparator 365 is needed. The overall probe will also be less expensive since two force sensors are much less expensive than one LVDT. Furthermore, alignment of the cable and tolerances associated with cable length are less critical when force sensors are used, and assembly of the unit is also made easier.

Figure 13:
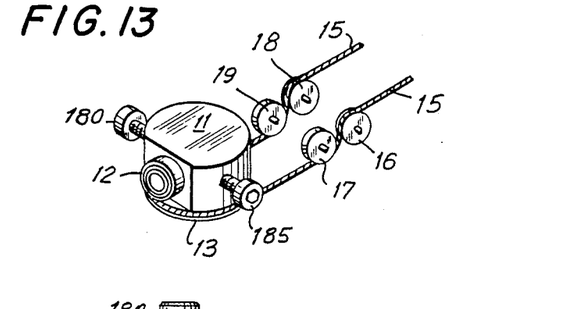
FIGS. 13 to 15 are illustrations of means for mechanically adjusting the resonant frequency of the scanning system, with FIG. 14 being a top view of the apparatus of FIG. 13.
Figure 14:
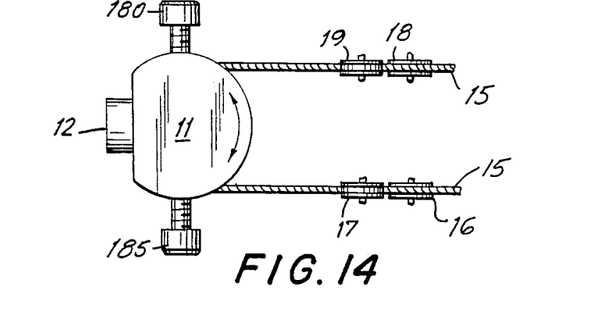
Figure 15:
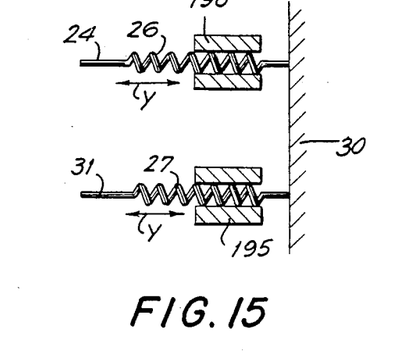

Referring now to FIGS. 13-15, various means for adjusting the resonant frequency of the apparatus are dislcosed. Where similar components are described as in FIG. 1, the same numerical designations are used.

The frequency of mechanical resonance is a function of the spring 26,27 constants, the geometry and material of the scanning head, the ultrasonic transducer mass 12 and the elasticity of the cable 15. The principal components of this frequency are the spring constants and scanner head geometry and material, all of which can be carefully controlled during the manufacture of the apparatus. The ultrasonic transducer mass and cable elasticity, however, cannot be controlled so easily, and can effect the resonant frequency to a significant degree to cause control problems when stable operation of the apparatus is required, particularly when operation at a precise frequency is desired. Therefore, a means for easily adjusting and precisely fixing the frequency of the system is important and necessary to obtain highly stable proper operation of the apparatus.

FIGS. 13 and 14 show a variation of the scanner head 11 of FIG. 1 wherein two heavy screws 180, 185 are added to the scanning head 11 and positioned along its diameter. Turning these screws 180, 185 into the head will lower the moment of inertia, thus raising the resonant frequency of the apparatus. Similarly, turning these screws outwardly will lower the frequency.

This effect can be mathematically expressed as:

$$f_o = \frac{1}{2\pi} \sqrt{\frac{(K_R + K_L)}{\left(M_T + \left(\frac{J_M + J_S}{R^2}\right)\right)}} \quad (13)$$

where $J_m$ is the moment of the scanning head and $J_s$ is the moment of inertia of the screws 180, 185.

There are other ways of providing such adjusting means to the apparatus. For example, FIG. 15 shows that the effective length of springs 26, 27 can be changed by a sliding collar 190, 195 on one or both of the springs 26, 27 to inhibit motion over a certain portion of the spring coils. When the effective spring length is changed, the equation for resonant frequency becomes:

$$f_o = \frac{1}{2\pi} \sqrt{\frac{K_R(y) + K_L(y)}{\left(M_T + \frac{J_M}{R^2}\right)}} \quad (14)$$

where $K_L(y)$ and $K_R(y)$ are the spring constants for length y.

For a larger size scanning apparatus, a series of weights or other masses can be used instead of screws 180, 185 to adjust the resonant frequency of the system. As noted above, adding weights would raise the frequency of the system, while removing weight would lower the frequency.

While it is apparent that the invention wherein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A scanning apparatus comprising:
    (A) means for obtaining information from an object;
    (B) means for oscillating said information obtaining means comprising:
    (i) frame means for providing support;
    (ii) means for connecting said information obtaining means to said frame means comprising:
        (a) transfer means at least partially comprising a cable for transmitting oscillating force to said information obtaining means;
        (b) means for providing bidirectional biasing forces comprising at least one spring to oscillate said transfer means;
        (c) means for measuring the displacement of a portion of said transfer means in response to the force providing means;
        (d) means for comparing the measured displacement of said transfer means portion with a predetermined desired displacement of said transfer means portion; and
        (e) means for providing driving forces to said transfer means comprising at least one solenoid to compensate for difference between said measured displacement and said predetermined desired displacement so that the information obtaining means is oscillated and scans a predetermined portion of said object;

(C) housing means surrounding said oscillation means; said housing means further containing a heat transfer fluid therein for damping vibrations associated with said apparatus; and (D) means for mounting to said housing means said information obtaining means and said oscillating means.

2. The apparatus of claim 1 wherein the biasing and driving force providing means each comprises means for providing linear movement.

3. The apparatus of claim 1 wherein the biasing force providing means comprises two separate springs and the driving force providing means comprises two separate solenoids.

4. The apparatus of claim 1 wherein said displacement measuring means is a transformer, and said comparison means comprises at least one comparator.

5. The apparatus of claim 1 wherein said oscillation means comprises means to reversibly rotate said information obtaining means through a predetermined angle.

6. The apparatus of claim 1 wherein said information obtaining means comprises an ultrasonic transducer.

7. The apparatus of claim 1 further comprising means for adjusting the resonant frequency of the apparatus.

8. A scanning apparatus comprising:
(A) means for obtaining information from an object;
(B) means for oscillating said information means comprising:
 (i) frame means for providing support;
 (ii) means for connecting said information obtaining means to said frame means comprising:
  (a) transfer means at least partially comprising a cable for transmitting oscillating force to said information obtaining means;
  (b) means attached to said frame for providing bidirectional biasing forces comprising at least one spring to oscillate said transfer means;
  (c) means for measuring the displacement of a portion of said transfer means in response to the biasing force providing means;
  (d) means for comparing the measured displacement of said transfer means portion with a predetermined desired displacement of said transfer means portion; and
  (e) means for providing driving forces to said transfer means comprising at least one solenoid to compensate for the difference between said measured displacement and said predetermined desired displacement so that the information obtaining means scans a predetermined portion of said object.

9. The apparatus of claim 8 wherein said biasing force providing means comprises a first spring for providing forces for linear movement in a first direction and a second spring for providing forces for linear movement in a direction opposite to that of the first direction.

10. The apparatus of claim 8 wherein said driving force providing means comprises first and second solenoids for compensating for the difference between said predetermined desired displacement and said measured displacement, said first and second solenoids operatively associated to produce forces in opposite directions.

11. The apparatus of claim 8 wherein said displacement measurement means is a transformer.

12. The apparatus of claim 8 wherein said driving force providing means comprises a single solenoid for providing forward and rearward linear movement forces.

13. The apparatus of claim 8 wherein the transfer means further comprises pulley means for rotating said object information obtaining means.

14. The apparatus of claim 13 wherein the object information obtaining means rotates back and forth through a predetermined angle.

15. The apparatus of claim 8 wherein the object information obtaining means linearly moves back and forth across a predetermined distance.

16. The apparatus of claim 15 wherein the connection means further comprises counterweight means to prevent vibration of the object information obtaining means.

17. The apparatus of claim 8 wherein the displacement measurement means comprises means for sensing forces.

18. The apparatus of claim 8 further comprising means for adjusting the frequency of the apparatus.

19. The apparatus of claim 8 wherein the object information obtaining means is an ultrasonic transducer.

20. The apparatus of claim 8 wherein said oscillation means comprises means to reversibly rotate said information obtaining means through a predetermined angle.

21. The apparatus of claim 18 wherein the frequency adjusting means comprises at least one screw located on said information obtaining means.

22. The apparatus of claim 18 wherein the frequency adjusting means comprises a collar attached to said biasing force providing means.

23. The apparatus of claim 8 further comprising means for surrounding and mounting said information obtaining means and said oscillating means.

24. The apparatus of claim 23 wherein said mounting means comprises housing means for containing a heat transfer fluid therein for damping the resonant vibration of the apparatus.

25. A method for obtaining information from an object which comprises constructing the apparatus of claim 1 and oscillating said information obtaining means at the resonant frequency of the apparatus such that said information obtaining means scans a proximate object and obtains information therefrom by transmitting a signal to said proximate object and receiving a reflected signal from said proximate object.

26. A method for obtaining information from an object which comprises constructing the apparatus of claim 8 and oscillating said information obtaining means at the resonant frequency of the apparatus such that said information obtaining means scans a proximate object and obtains information therefrom by transmitting a signal to said proximate object and receiving a reflected signal from said proximate object.

27. The method of claim 25 which further comprises adjusting the frequency of the apparatus prior to oscillating said information obtaining means.

28. The method of claim 26 which further comprises adjusting the frequency of the apparatus prior to oscillating said information obtaining means.

29. A scanning apparatus comprising:
(a) a frame;
(b) transducer means for obtaining information from an object to be scanned, said transducer means being mounted for oscillatory movement with respect to said frame;

(c) biasing means comprising at least one spring attached to said frame for providing a bidirectional biasing force;
(d) cable means attached to said biasing means and in frictional contact with said transducer means for providing said oscillatory movement of said transducer means and biasing of said biasing means;
(e) measurement means for measuring linear displacement of said cable means;
(f) comparison means for comparing said linear displacement of said cable means as measured by said measurement means to a predetermined desired linear displacement of said cable means; and
(g) means for providing a linear driving force to said cable means in order to compensate for a difference between said linear displacement of said cable means as measured by said measurement means and said predetermined desired linear displacement of said cable means.

30. The apparatus of claim 29 further comprising means for housing at least one of said frame, said transducer means, said biasing means, said cable means, said measurement means, said comparison means and said driving means.

31. The apparatus of claim 30 wherein said housing means also encloses a heat transfer fluid for damping said oscillatory movement.

32. The apparatus of claim 29 wherein said measurement means is a transformer and said comparison means is a comparator.

33. The apparatus of claim 29 wherein said oscillatory movement comprises oscillatory rotation of said transducer means through a predetermined angle wherein said oscillatory movement is associated with biasing of said biasing means.

34. The apparatus of claim 29 wherein said oscillatory movement comprises oscillatory linear movement of said transducer means along a predetermined length wherein said oscillatory movement is associated with biasing of said biasing means.

35. The apparatus of claim 29 wherein said transducer means is an ultrasonic transducer.

36. The apparatus of claim 29 further comprising means for adjusting the operational frequency associated with said apparatus.

37. The apparatus of claim 29 wherein the frequency of said oscillatory movement is the resonant frequency associated with said apparatus.

38. A method for obtaining information from an object which comprises constructing the apparatus of claim 29 and oscillating said information obtaining means at the resonant frequency of the apparatus such that said information obtaining means scans a proximate object and obtains information therefrom by transmitting a signal to said proximate object and receiving a reflected signal from said proximate object.

39. The method of claim 38 which further comprises adjusting the frequency of the apparatus prior to oscillating said information obtaining means.

40. A scanning apparatus for scanning an object back and forth while transmitting sound waves to the object and receiving reflected sound waves from the object comprising:
(a) a frame;
(b) an ultrasonic transducer mounted to said frame for oscillatory movement with respect to said frame and for obtaining information from said object to be scanned;
(c) a spring attached to said frame for providing a bidirectional biasing force;
(d) a cable attached to said spring and in frictional contact with said ultrasonic transducer for providing said oscillatory movement of said ultrasonic transducer and biasing of said spring;
(e) a transformer in close proximity to a portion of said cable for measuring linear displacement of said cable;
(f) a comparator for comparing said linear displacement of said cable as measured by said transformer to a predetermined desired linear displacement of said cable;
(g) a solenoid for providing a linear driving force to said cable in order to compensate for a difference between said linear displacement of said cable as measured by said comparator and said predetermined desired linear displacement of said cable;
(h) adjusting means for adjusting the resonant frequency associated with said apparatus; and
(i) housing means for housing at least one of the group of said frame, said ultrasonic transducer, said spring, said cable, said transformer, said comparator, and said solenoid, said housing means also enclosing a heat transfer fluid for damping said oscillatory movement,
wherein the frequency of said oscillatory movement is said resonant frequency associated with said apparatus.

41. The apparatus of claim 40 wherein said oscillatory movement comprises oscillatory rotation of said ultrasonic transducer through a predetermined angle wherein said oscillatory movement is associated with biasing of said spring.

42. The apparatus of claim 40 wherein said oscillatory movement comprises oscillatory linear movement of said ultrasonic transducer along a predetermined length wherein said oscillatory movement is associated with biasing of said spring.

43. A method for obtaining information from an object which comprises constructing the apparatus of claim 40 and oscillating said transducer means at the resonant frequency of the apparatus such that said transducer means scans a proximate object and obtains information therefrom by transmitting a signal to said proximate object and receiving a reflected signal from said proximate object.

44. The method of claim 43 further comprising adjusting the resonant frequency associated with said apparatus.

45. The method of claim 43 further comprising adjusting said adjusting means in order to alter the resonant frequency associated with said apparatus.

46. A scanning apparatus comprising:
(a) a frame;
(b) transducer means for obtaining information from an object to be scanned, said transducer means being mounted for oscillatory movement with respect to said frame;
(c) biasing means attached to said frame for providing a bidirectional biasing force;
(d) cable means attached to said biasing means and in frictional contact with said transducer means for providing said oscillatory movement of said transducer means and biasing of said biasing means;
(e) measurement means for measuring linear displacement of said cable means;
(f) comparison means for comparing said linear displacement of said cable means as measured by said measurement means to a predetermined desired linear displacement of said cable means; and (g) means comprising at least one solenoid for providing a linear driving force to said cable means in order to compensate for a difference between said linear displacement of said cable means as measured by said measurement means and said predetermined desired linear displacement of said cable means.

47. The apparatus of claim 46 further comprising means for housing at least one of said frame, said transducer means, said biasing means, said cable means, said measurement means, said comparison means and said driving means.

48. The apparatus of claim 47 wherein said housing means also encloses a heat transfer fluid for damping said oscillatory movement.

49. The apparatus of claim 46 wherein said biasing means is a spring and wherein said transducer means is an ultrasonic transducer.

50. The apparatus of claim 46 wherein the measurement means is a transformer and said comparison means is a comparator.

51. The apparatus of claim 46 wherein said oscillatory movement comprises oscillatory rotation of said transducer means through a predetermined angle wherein said oscillatory movement is associated with the biasing of said biasing means.

52. The apparatus of claim 46 wherein said oscillatory movement comprises oscillatory linear movement of said transducer means along a predetermined length wherein said oscillatory movement is associated with biasing of said biasing means.

53. The apparatus of claim 46 further comprising means for adjusting the operational frequency associated with said apparatus.

54. The apparatus of claim 46 wherein the frequency of said oscillatory movement is the resonant frequency associated with said apparatus.

* * * * *